(12) United States Patent
Lommel et al.

(10) Patent No.: US 6,433,248 B1
(45) Date of Patent: Aug. 13, 2002

(54) TRANS-ACTIVATION OF TRANSCRIPTION FROM VIRAL RNA

(75) Inventors: Steven A. Lommel, Cary; Timmy L. Sit, Raleigh, both of NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/088,274

(22) Filed: Jun. 1, 1998

(51) Int. Cl.$^7$ .................. C12N 15/82; C12N 15/83; C12N 15/84; A01H 5/00; A01H 5/10

(52) U.S. Cl. ................ 800/278; 435/69.1; 435/320.1; 435/468; 435/469; 435/470; 536/23.1; 800/288; 800/292; 800/293; 800/294; 800/298; 800/301

(58) Field of Search ................ 435/69.1, 320.1, 435/410, 418, 419, 468, 470, 469; 536/24.1, 23.72, 23.1; 800/278, 279, 288, 292, 293, 295, 298, 301, 302, 294

(56) References Cited

PUBLICATIONS

Jeong et al, J. Virol., vol. 68, pp. 2615–2623, 1994.*
Bates; Electroporation of Plant Protoplasts and Tissues, *Methods In Cell Biology*, 50:363–373 (1995).
Brisson et al.; Expression of a bacterial gene in plants by using a viral vector, *Nature*, 310:511–514 (1984).
Düring et al.; Synthesis and self–assembly of a functional monoclonal antibody in transgenic *Nicotiana tabacum*, *Plant Molecular Biology*, 15:281–293 (1990).
Mariani et al.; Induction male sterility in plants by a chimaeric ribonuclease gene, *Nature*, 347:737–741 (1990).
Miki et al.;Procedures for Introducing Foreign DNA into Plants, *Methods in Plant Molecular Biology and Biotechnology*, Chapter 6:67–88 (1993).
Opperman et al.; Root–Knot Nematode—Directed Expression of a Plant Root–Specific Gene, *Science*, 263:221–223 1994.
Siegel et al.; Sequence–specific recognition of a subgenomic RNA promoter by a viral RNA polymerase, *Proc. Natl. Acad. Sci. USA*, 94:11238–11243 (1997).
Sit, et al.;RNA—Mediated Trans–Activation of Transcription from a Viral RNA, *Science*, 281:829–832 (1998).
Xiong et al.; The Complete Nucleotide Sequence and Genome Organization of Red Clover Necrotic Mosaic Virus RNA—1, *Virology*, 171:543–554 (1989).
Zavriev et al.; Mapping of the Red Clover Necrotic Mosaic Virus Subgenomic RNA, *Virology*, 216:407–410 (1996).

PCT International Search Report for International application No. PCT/US99/10533 (Sep. 29, 1999).
Sit et al.; RNA—Mediated Trans–Activation of Transcription from a Viral RNA, *Science*, 281:829–832 (Aug. 7, 1998 Reprint Series).
Zavriev et al.; Mapping of the Red Clover Necrotic Mosaic Virus Subgenomic RNA, *Virology*, 216 (Article No. 0076):407–410 (1996).
Vaewhongs et al.; Virion Formation I s Required for the Long–Distance Movement of Red Clover Necrotic Mosaic Virus in Movement Protein Transgenic Plant, *Virology*, 212:607–613 (1995).
Maia et al.; Gene Expression from Viral RNA Genomes, *Plant Molecular Biology*, 32:367–391 (1996).
Zaccomer et al.; The Remarkable Variety of Plant RNA Virus Genomes, *J. of General Virology*, 76:231–247 (1995).
Miller et al.; Synthesis of Brome Masaic Virus Subgenomic RNA In Vitro by Internal Initiation on (–)–Sense Genomic RNA, *Nature*, 313:68–70 (Jan. 3, 1985).
Miller et al.; Luteovirus Gene Expression, *Critical Reviews in Plant Sciences*, 14(3):179–211 (1995).
Yutaka Eguchi et al.; Antisense RNA, *Annu. Rev. Biochem.*, 60:631–652 (1991).
Siegel et al.; Sequence–Specific Recognition of a Subgenomic RNA promoter by a Viral RNA Polymerase, *Proc. Natl. Acad. Sci. USA*, 94:11238–11243 (Oct. 1997).
Lai et al.; The Molecular Biology of Coranaviruses; *Advances in Virus Research*, 48:1–100 (1997).

* cited by examiner

Primary Examiner—Amy J. Nelson
Assistant Examiner—Ashwin Mehta
(74) Attorney, Agent, or Firm—Myers Bigel Sibley & Sajovec (57) ABSTRACT

A method of activating transcription of an RNA of interest in a cell (e.g., a dicot plant cell) includes the steps of: (a) providing a host cell containing a heterologous construct, the heterologous construct comprising an RNA virus subgenomic promoter operatively associated with a heterologous RNA of interest, wherein the promoter does not initiate transcription of the heterologous RNA in the absence of a corresponding RNA virus trans-activating RNA segment, and wherein the RNA virus trans-activating RNA segment is absent from the host cell; and then (b) introducing a transactivating nucleic acid segment into the host cell so that transcription of the heterologous RNA is initiated. The trans-activating segment may be introduced into the cell by any suitable means, such as by infecting the cell with a virus, which virus expresses the trans-activating RNA.

29 Claims, 6 Drawing Sheets

(1 of 6 Drawing Sheet(s) Filed in Color)

TRANS-ACTIVATION OF TRANSCRIPTION FROM VIRAL RNA

This invention was made with Government support under grant number MCB-9419700 from the National Science Foundation. The Government has certain rights to this invention.

FIELD OF THE INVENTION

The present invention concerns inducible promoters and trans-activators for such inducible promoters, along with recombinant organisms such as plants containing the same.

BACKGROUND OF THE INVENTION

RNA has been shown to perform many of the functions that were once thought restricted to proteins. RNA molecules can function as nucleases, as demonstrated by the self-cleavage of RNA introns and the catalytic RNA of RNase P (K. Kruger et al., *Cell* 31, 147 (1982); S. Altman, L. Kirsebom, S. Talbot, *FASEB J.* 7, 7 (1993)). RNA molecules can also catalyze peptide bond formation and perform the functions of a kinase, a ligase and an RNA polymerase (B. Zhang and T. R. Cech, *Nature* 390, 96 (1997); J. R. Lorsch and J. W. Szostak, *Nature* 371, 31 (1994); E. H. Ekland, J. W. Szostak, D. P. Bartel, *Science* 269, 364 (1995); J. A. Doudna, S. Couture, J. W. Szostak, *Science* 251, 1605 (1991)). Given this diversity of functions, it is not surprising that mRNAs themselves can mediate gene expression at the translational level (D. R. Gallie, *Plant Mol. Biol.* 32, 145 (1996)).

Non-coding RNAs as well as the 3' untranslated regions (3' UTR) of cellular mRNAs have also been shown to function as trans-acting regulators (riboregulators) of cell division and differentiation (F. Rastinejad, M. J. Conboy, T. A. Rando, H. M. Blau, *Cell* 75, 1107 (1993); M. D. Crespi et al, *EMBO J.* 13, 5099 (1994); C. J. Decker and R. Parker, *Curr. Opin. Cell Biol.* 7, 386 (1995); E. R. Jupe et al., *Cell Growth & Diff.* 7, 871 (1996)). In *Caenorhabditis elegans,* the small non-coding lin-4 RNAs can interact with the 3' UTR of lin-14 mRNAs to alter gene expression by affecting their stability and/or translatability (R. C. Lee, R. L. Feinbaum, V. Ambros, *Cell* 75, 843 (1993); B. Wightnan, I. Ha, G. Ruvkin, *Cell* 75, 855 (1993)). Surprisingly, however, the regulation of RNA transcription by another RNA species has not been observed.

SUMMARY OF THE INVENTION

A method of activating transcription of an RNA of interest in a cell, in vitro or in vivo, comprises: (a) providing a host cell containing a heterologous construct, the heterologous construct comprising an RNA virus subgenomic promoter operatively associated with a heterologous RNA of interest, wherein the promoter does not initiate transcription of the heterologous RNA in the absence of a corresponding RNA virus trans-activating RNA segment, and wherein the RNA virus trans-activating RNA segment is absent from the host cell; and then (b) introducing a trans-activating nucleic acid segment into the host cell so that transcription of the heterologous RNA is initiated. The cell is preferably a plant cell, such as a dicot plant The trans-activating segment may be introduced into the cell by any suitable means, such as electroporation, by infecting the cell with a virus, which virus expresses the trans-activating RNA, or by even adding the segment to a culture solution containing plants or plant cells in vitro in which heterologous proteins are being produced.

A second aspect of the invention is an isolated nucleic acid encoding an RNA virus trans-activating RNA (e.g., an RNA or a DNA such as a cDNA encoding the RNA, or a synthetic oligonucleotide). Examples of such nucleic acids include:

(a) an RNA containing the sequence: UCAAUCAGAG-GUAUCGCCCCGCCUCUCAGUGUUG (SEQ ID NO:1)

(b) an RNA containing the sequence: AGAGGUAUCGC-CCCGCCUCUC (SEQ ID NO:2); and (c) a DNA encoding an RNA of (a) or (b) above. The nucleic acid is preferably at least 15, 18 or 20 nucleotides in length, and in one embodiment is preferably not more than 40, 50 or 60 nucleotides in length. In another embodiment, the nucleotide may be incorporated into a longer molecule up to 400, 500, or 600 nucleotides in length or more. Fragments of (a) to (c) above which retain trans-activating activity are thus included within the invention. The nucleic acids may be incorporated into constructs of the foregoing operatively associated with a heterologous promoter (e.g., an inducible promoter), and the constructs provided on vectors for transient transfection or stable transformation of host cells as described in greater detail below.

Also disclosed is a method of activating transcription of an RNA of interest in a plant. The method comprises: (a) transforming a plant cell with a vector comprising heterologous construct, the heterologous construct comprising a plant RNA virus subgenomic promoter operatively associated with a heterologous nucleic acid of interest to provide a transformed plant cell, wherein the promoter does not initiate transcription of the heterologous nucleic acid in the absence of a corresponding RNA virus trans-activating RNA segment, and wherein the RNA virus trans-activating RNA segment is absent from the plant cell; then (b) regenerating a plant from the transformed plant cell; and then (c) infecting the plant with a viral or bacterial vector that transcribes the trans-activating RNA segment in the cells of the plant so that transcription of the heterologous nucleic acid in the cells of the plant is initiated. The transforming step may be carried out by any suitable means, but is preferably carried out in a manner that causes the heterologous construct to be stably integrated into the genome of the plant. Suitable means include transformation with ballistic vectors, electroporation, transformation with Agrobacterium vectors such as *Agrobacterium tumefaciens* or *Agrobacterium rhizogenes* vectors, and with DNA virus vectors. The infecting step may likewise be carried out by any suitable means, such as with an with an RNA virus vector, a DNA virus vector, or an Agrobacterium vector.

The invention is explained greater detail in the drawings herein and the specification below.

BRIEF DESCRIPTION OF THE DRAWINGS

The file of this patent contains at least one drawing executed in color. Copies of this patent with color drawings will be provided by the PTO upon request and payments of the necessary fee.

FIG. 1(A–B). RCNMV RNA-1 expresses sGFP only in the presence of RNA-2 constructs.

FIG. 1B. Schematic diagram of RCNMV RNA-2 and RNA-2 derivatives. R2ΔATG contains a deletion of the MP start codon and does not produce functional MP. R2(GFP) is a construct where the MP is precisely replaced with the wild-type GFP ORF (shaded box). R2GΔH is a construct derived from R2(GFP) where 225 3' terminal nucleotides of the GFP ORF are replaced by 324 3' terminal nucleotides from the MP ORF (dotted lines). R2GΔHX is a construct derived from R2GΔH with a 120-nucleotide deletion of the 3' terminal MP ORF sequence.

FIG. 2(A–B). TBSV expressing appropriate RCNMV RNA-2 sequences can activate transcription in trans from the CP subgenomic promoter on RCNMV RNA-1.

FIG. 3(A–C). Analysis of RCNMV RNA-1 sgRNA synthesis and CP gene expression utilizing RCNMV RNA-2 sequences expressed from the TBSV replicon.

FIG. 3A. Western blot analysis of CP production. Total *Nicotiana benthamiana* leaf proteins were extracted 3 days post inoculation, electrophoresed and transferred to nitrocellulose membranes. The membrane was subsequently probed with polyclonal antisera to the RCNMV CP. Lanes are from tissues inoculated with: 1, mock; 2, wild-type RCNMV; 3. RCNMV RNA-1 co-inoculated with pHST2; 4, RCNMV RNA-1 co-inoculated with pHST2-SL2.

FIG. 3C. Northern blot hybridization analysis of R1sGFP/pHST2 co-inoculations. Total RNA was extracted from *Nicotiana clevelandii* leaves 3 days post-inoculation, electrophoresed on 1% denaturing agarose gels and transferred to nylon membranes. The membrane was probed with an sGFP specific $^{32}$P-labelled DNA. Position of genomic R1sGFP and sgRNA are identified. Premature termination products of viral replication are visible as a smear in lanes 2–4. Lanes are as follows: 1, mock; 2, R1sGFP+pHST2; 3, R1sGFP+pHST2-SL2; 4, R1sGFP+RNA-2.

FIG. 4(A–B). Fluorescence microscopy of sGFP expression from RCNMV RNA-1. Images are representative of infections 3 days post-inoculation on *Nicotiana benthamiana*. Leaves were viewed with a Leica MZ12 Stereo Microscope with a Fluorescence Module and the GFP Plus Filter Set (480 nm excitation/510 nm emission).

FIG. 5(A–B). Model of the trans-activation mechanism utilized by RCNMV to generate a sgRNA from RNA-1 with the help of RNA-2.

FIG. 5B. A model for the generation of the CP sgRNA is shown. Complementary-strand synthesis proceeds until the 8-nucleotide base-paired region between RNA-1 and RNA-2 is encountered. This structure periodically forces the polymerase to disengage from the genomic-sense template releasing a premature complementary strand that has the polymerase recognition sequence exposed on its 3' end (gray box in inset). This then acts as template for the production of a genomic-sense CP sgRNA, which is the monocistronic template for CP translation.

DETAILED DESCRIPTION OF THE INVENTION

The present invention now will be described more fully hereinafter with reference to the accompanying Figures, in which certain embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Nucleotide sequences are presented herein by single strand only, in the 5' to 3' direction, from left to right. Amino acid sequences disclosed herein are presented in the amino to carboxy direction, from left to right, unless otherwise indicated. The amino and carboxy groups are not presented in the sequence. Nucleotides and amino acids are represented herein in the manner recommended by the IUPAC-IUB Biochemical Nomenclature Commission.

As used herein, the terms "protein" and "polypeptide" are used interchangeably, and refer to a polymer of amino acids (dipeptide or greater) linked through peptide bonds. Thus, the term "polypeptide" includes proteins, oligopeptides, protein fragments, protein analogs and the like. The term "polypeptide" contemplates polypeptides as defined above that are encoded by nucleic acids, are recombinantly produced, are isolated from an appropriate source, or are synthesized.

RNA viruses used to carry out the present invention (as sources of promoters and corresponding trans-activators) are preferably bipartite RNA viruses, and are preferably a plant virus such as a Dianthovirus. Dianthoviruses include, but are not limited to, red clover necrotic mosaic virus, carnation ringspot virus, sweet clover necrotic mosaic virus, furcraea necrotic streak virus, and others such as sesame dianthovirus. the subgenomic promoter may be of any type, but in one embodiment is a capsid protein promoter. The trans-activator may be from the same or different virus as the corresponding subgenomic promoter (e.g., both may be from a dianthovirus, but from a different dianthovirus).

An RNA polymerase that transcribes RNA from the subgenomic promoter and heterologous RNA is preferably included in the cell for transcription of the RNA of interest. The RNA polymerase may be from the same or different organism as the subgenomic promoter and/or the trans-activating RNA segment. (e.g., the polymerase may be from the same or different dianthovirus as either, or both, the subgenomic promoter and the trans-activating RNA segment). The RNA polymerase may be introduced into the cell prior to introduction of the trans-activating segment (for example, concurrently with the heterologous construct), may be introduced concurrently with introduction of the trans-activating segment (for example, by co-expression from the vector that expresses the trans-activating segment), or may be introduced into the cell after introduction of the trans-activating segment.

Nucleotide sequences encoding the novel trans-activators are also provided. Specific trans-activators are disclosed herein as SEQ ID NO:1 and SEQ ID NO:2. Methods are readily available in the art for the hybridization of nucleic acid sequences. Sequences that code for trans-activators may be isolated according to well known techniques based on their sequence homology to SEQ ID NO:1 or SEQ ID NO:2 herein. In these techniques, all or part of the known sequence is used as a probe which selectively hybridizes to other trans-activator sequences present in a population of nucleic acid fragments from a chosen organism. See, e.g.. Sambrook et al., *Molecular Cloning*, eds., Cold Spring Harbor Laboratory Press (1989). For example, hybridization of such sequences may be carried out under conditions of reduced stringency, medium stringency or even stringent conditions (e.g., conditions represented by a wash stringency of 35–40% Formamide with 5×Denhardt's solution, 0.5% SDS and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively), to DNA encoding resistance to trans-activators disclosed herein in a standard hybridization assay. See J. Sambrook et al., *Molecular Cloning, A Laboratory Manual 2d Ed.* (1989) Cold Spring Harbor Laboratory. In general, sequences which code for a trans-activator and hybridize to the segment disclosed as SEQ ID NO:1 or SEQ ID NO:2 will be at least 50% homologous, 60% homologous, 70% homologous, or even 85% homologous or more therewith. That is, the sequence similarity of sequences may range, sharing at least about 50%, 60%, 70%, and even about 85%, 90%, 95% or more sequence similarity.

The nucleotide sequences of the invention are useful in the genetic manipulation of organisms, including bacteria, fungi, yeast, plants and animals and cells thereof. This aspect of the invention is illustrated herein with respect to the genetic manipulation of plants. In this manner, the nucleotide sequences of the present invention are provided in expression cassettes for expression in the plant of interest. The cassette will include 5' and 3' regulatory sequences operably linked to the gene of interest. The term "operably linked," as used herein, refers to DNA sequences on a single DNA molecule which are associated so that the function of one is affected by the other. Thus, a promoter is operatively associated with a gene of the present invention when it is capable of affecting the expression of the gene of the present invention (i.e., the gene is under the transcriptional control of the promoter). The promoter is said to be "upstream" from the gene, which is in turn said to be "downstream" from the promoter.

Expression cassettes of the present invention include, 5'–3' in the direction of transcription, a promoter as discussed above, a nucleic acid of interest (e.g., one encoding a protein or peptide) operatively associated with the promoter, and, optionally, a termination sequence including stop signal for RNA polymerase and a polyadenylation signal for polyadenylase (e.g., the nos terminator). All of these regulatory regions should be capable of operating in the cells to be transformed.

In preparing the expression cassette, the various nucleic acid fragments may be manipulated, so as to provide for the nucleic acid sequences in the proper orientation and, as appropriate, in the proper reading frame. Towards this end, adapters or linkers may be employed to join the fragments or other manipulations may be involved to provide for convenient restriction sites, removal of superfluous DNA, removal of restriction sites, or the like. For this purpose, in vitro mutagenesis, primer repair, restriction, annealing, resection, ligation, PCR, or the like may be employed, where insertions, deletions or substitutions, e.g. transitions and transversions, may be involved.

The compositions and methods of the present invention can be used to transform any plant, or any portion of a plant thereof. In this manner, genetically modified plants, plant cells, plant tissue (e.g., plant leaves, stems, roots), seeds, seed coats, and the like can be obtained. Transformation protocols may vary depending on the type of plant or plant cell, i.e. monocot or dicot, targeted for transformation. Suitable methods of transforming plant cells include microinjection (Crossway et al. (1986) Biotechniques 4:320–334), electroporation (D'Halluin et al., 5,712,135 (Monocots); Riggs et al. (1986) *Proc. Natl. Acad. Sci. USA,* 83:5602–5606), *Agrobacterium* mediated transformation (Hinchee et al. (1988) *Biotechnology,* 6:915–921), direct gene transfer (Paszkowski et al. (1984) *EMBO J.,* 3:2717–2722), and ballistic particle acceleration (see, for example, Sanford et al., U.S. Pat. No. 4,945,050; WO91/10725 and McCabe et al. (1988) *Biotechnology,* 6:923–926). Also see, Weissinger et al. (1988) *Annual Rev. Genet.,* 22:421–477; Sanford et al. (1987) *Particulate Science and Technology,* 5:27–37 (onion); Christou et al. (1988) *Plant Physiol.* 87:671–674(soybean); McCabe et al. (1988) *Bio/Technology,* 6:923–926 (soybean); Datta et al. (1990) *Biotechnology,* 8:736–740 (rice); Klein et al. (1988) *Proc. Natl. Acad. Sci. USA,* 85:4305–4309(maize); Klein et al. (1988) *Biotechnology,* 6:559–563 (maize); WO91/10725 (maize); Klein et al. (1988) *Plant Physiol.,* 91:440–444 (maize); Fromm et al. (1990) *Biotechnology,* 8:833–839; and Gordon-Kamm et al. (1990) *Plant Cell,* 2:603–618 (maize); Hooydaas-Van Slogteren & Hooykaas (1984) *Nature* (London), 311:763–764; Bytebier et al. (1987) *Proc. Natl. Acad. Sci. USA,* 84:5345–5349 (Liliaceae); De Wet et al. (1985) In *The Experimental Manipulation of Ovule Tissues,* ed. G. P. Chapman et al., pp. 197–209. Longman, N.Y. (pollen); Kaeppler et al. (1990) *Plant Cell Reports,* 9:415418; and Kaeppler et al. (1992) *Theor. Appl. Genet.,* 84:560–566 (whisker-mediated transformation); D'Halluin et al. (1992) *Plant Cell,* 4:1495–1505 (electroporation); Li et al. (1993) *Plant Cell Reports,* 12:250–255 and Christou and Ford (1995) *Annals of Botany,* 75:407413 (rice); Osjoda et al. (1996) *Nature Biotechnology,* 14:745–750 (maize via *Agrobacterium tumefaciens*); all of which are herein incorporated by reference.

The vector may be a viral vector, including both RNA viruses and DNA viruses. DNA viruses are preferred where stable integration of the heterologous segment into the genome of the cell being transformed is desired. Any plant viral vector can be used, including but not limited to those described in Donson et al., U.S. Pat. No. 5,316,93 1; Donson et al., U.S. Pat. No. 5,589,367; Morinaga et al., U.S. Pat. No. 4,855,237; Brisson et al., Expression of a bacterial gene in plants by using a viral vector, Nature 310, 511–514 (1984); Brisson and Holin, Plant virus vectors: cauliflower mosaic virus, Methods in Enzymology 118, 659–668 (1986); Ahlquist and French, Multicomponent RNA plant virus infection derived from cloned viral cDNA, Proc. Natl. Acad. Sci. USA 81: 7066–7070 (1984); Takamatusu et al., Expression of bacterial chloramphenicol acetyltransferase gene in tobacco plants mediated by TMV-RNA, The EMBO Journal 6, 307–311 (1987); French et al., Bacterial Gene Inserted in an Engineered RNA Virus: Efficient Expression in Monocotyledonous Plant Cells, Science 231, 1294–1297 (1986); Takamatsu et al., Production of enkephalin in tobacco protoplasts using tobacco mosaic virus RNA vector, FEBS Letters 269: 73–76 (1990). Viral infection can be mediated by an Agrobacterium in accordance with known techniques. Grimsley et al., Agrobacterium-mediated delivery of infectious maize streak virus into maize plants, Nature 325, 177–179 (1981); Elmer et al., Agrobacterium-mediated inoculation of plants with tomato golden mosaic virus DNA's, Plant Molecular biology 10, 225–234 (1988).

Plant species may be transformed with a DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants which may be employed in practicing the present invention include (but are not limited to) tobacco (*Nicotiana tabacum*), potato (*Solanum tuberosum*), soybean (glycine max), peanuts (*Arachis hypogaea*), Brassica species (e.g., rape, canola), sorghum (*Sorghum bicolor*), cotton (*Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), Cashew (*Anacardium occidentale*), macadamia (*Macadamia integrifolia*), almond (*Prunus amygdalus*), sugar beets (*Beta vulgaris*), corn (*Zea mays*), wheat, oats, rye, barley, rice, vegetables, ornamentals, and conifers. Vegetables include tomatoes (*Lycopersicon esculentum*), carrots, asparagus, lettuce (e.g., *Lactuea sativa*), green beans (*Phaseolus vulgaris*), lima beans (*Phaseolus limensis*), peas (Lathyrus spp.) and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petnunias (*Petunia hybrida*), carnation (*dianthus caryophyllus*), poinsettia (*Euphorbia pulcherima*), and chyrsanthemum. Conifers which may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The cells which have been transformed may be grown into plants in accordance with conventional techniques. See, for example, McCormick et al. (1986) *Plant Cell Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved. Seeds that germinate into plants of the present invention can be collected and packaged for sale from such plants in accordance with known techniques. Thus plants of the present invention may take a variety of forms: The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species).

Cells of the present invention can be used to express heterologous proteins in industrial fermentation procedures. Such procedures can be carried out with any suitable cell, including plant and yeast cells as described above. Transcription of the nucleic acid of interest can be activated when desired; for example after a growth phase of the cell in the culture media is completed. Where such fermentation procedures are employed, the trans-activator may be contacted to the promoter by infecting the cells with a vector as described above, or a synthetic oligonucleotide (e.g., a DNA, RNA, or modified analog thereof such as a peptide nucleic acid) can be added to the culture media in accordance with known techniques.

Plants of the present invention can likewise be used to express such heterologous proteins or peptides (e.g., therapeutic proteins or peptides such as a mammalian protein or peptide, like human growth hormone or insulin). When plants are used, the present invention allows the heterologous protein to be expressed only when desired, thus preserving the option of harvesting the plant without expression of the heterologous protein or peptide (for example, when market conditions favor production of the heterologous protein or peptide rather than the plant itself). The heterologous protein or peptide could be one that imparts disease resistance to the plant, such as a *Bacillus thuringensis* protein or fragment thereof.

The present invention can also be used to provide a cascade control system by interposing the trans-activator and corresponding promoter between an inducible promoter and a nucleotide of interest to be transcribed by induction of the inducible promoter. Since inducible promoters can "leak" (that is, drive some transcription even in the absence of the appropriate stimulus), the provision of such a cascade control system allows tighter regulation of the nucleotide of interest. Such a method of activating transcription of an RNA of interest in a cell comprises (a) providing a cell containing a first heterologous construct and a second heterologous construct; the first heterologous construct comprising an inducible promoter operably associated with a nucleic acid segment encoding an RNA virus transactivating segment; the second heterologous construct comprising an RNA virus subgenomic promoter operatively associated with the heterologous RNA of interest, wherein the RNA virus subgenomic promoter does not initiate transcription of the heterologous RNA of interest in the absence of the RNA virus trans-activating RNA segment and initiates transcription of the heterologous RNA in the presence of the RNA virus trans-activating RNA segment; and then (b) inducing the inducible promoter so that transcription of the RNA virus trans-activating regulatory element is initiated, and transcription of the heterologous RNA in the cell is initiated.

A transgenic plant incorporating such a cascade control system comprises transformed plant cells, the transformed plant cells containing a first heterologous construct and a second heterologous construct as described above. Again, inducing the inducible promoter causes transcription of the RNA virus trans-activating regulatory element to be initiated, so that transcription of the heterologous RNA is initiated.

Any inducible promoter, and the corresponding inducing agent or stimulus, can be used to carry out the present invention in accordance with known techniques, including but not limited to nitrate reductase inducible promoters (nitrate induced), the 35S-tet promoter (tetracycline induced) heat shock protein promoters such as HSP70 promoters (heat induced), auxin responsive promoters, ethylene responsive promoters, jasmonic acid responsive promoters (responsive to wounding), PR (pathogen-related) promoters (salicyclic acid induced). In one embodiment, the promoter is a nematode-responsive promoter or nematode inducible promoter, and the nucleic acid of interest encodes a protein or peptide that disrupts nematode infection (e.g., a protein or peptide that is toxic to the plant cell); these embodiments may be carried out as described in U.S. Pat. No. 5,750,386 to Conkling or U.S. Pat. No. 5,589,622 to Gurr. In addition, cells and plants containing such cascade control systems can be used for the same purposes as described above.

The present invention is more fully illustrated by the following Examples, which are set forth to illustrate the present invention and are not to be construed as limiting thereof.

EXAMPLES

Figure 1A:
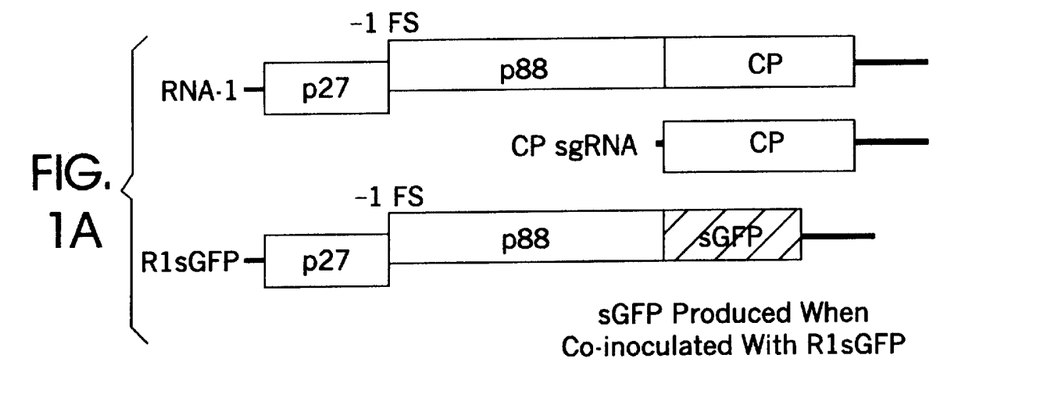
FIG. 1A. Schematic diagram of RCNMV RNA-1, capsid protein (CP) subgenomic RNA (sgRNA) and R1sGFP. ORFs for p27, the -1 ribosomal frameshift product p88 and the CP are labeled. R1sGFP is a construct where the CP is replaced with the sGFP ORF (shaded box). sGFP is expressed from this modified genomic RNA-1 only when a subgenomic RNA is generated.

RNA viruses display a wide diversity of gene expression mechanisms at both the transcriptional and translational levels (I. G. Maia, K. Seron, A.-L. Haenni, F. Bernard, *Plant Mol. Biol.* 32, 367 (1996). The bipartite genome of red clover necrotic mosaic dianthovirus (RCNMV) utilizes a -1 ribosomal frameshifting mechanism to express the viral polymerase, and subgenomic RNA (sgRNA) synthesis to express the capsid protein (CP) from the polycistronic RNA-1 (D. Giesman-Cookmeyer, K.-H. Kim, S. A. Lommel, in *Pathogenesis and Host-Parasite Specificity in Plant Diseases: Histopathological, Biochemical, Genetic and Molecular Basis,* Vol. III, U. S. Singh, R. P. Singh, K. Kohmoto, Eds. (Pergamon Press, Tarrytown, N.Y., 1995) pp. 157–176; see FIG. 1A). The generation of a sgRNA for CP expression is necessary since the CP is encoded by the 3' proximal open reading frame on RNA-1 and is therefore inaccessible to the eukaryotic translational machinery (M. Kozak, *J. Cell Biol.* 108, 229 (1989)). The monocistronic RNA-2 (see FIG. 1B) is directly translated to produce the viral movement protein (MP) required for the cell-to-cell spread of infection (Z. Xiong, K. H. Kim, D. Giesman-Cookmeyer, S. A. Lommel, *Virology* 192, 27 (1993); D. Giesman-Cookmeyer and S. A. Lommel, *Plant Cell* 5, 973 (1993)). Previous experiments have shown that RNA-1 is capable of independent replication in plant protoplasts (T. A. M. Osman and K. W. Buck, *J. Gen. Virol.* 68, 289 (1987); L. L. Paje-Manalo and S. A. Lommel, *Phytopathology* 79, 457 (1989)) and can produce a local infection on the inoculated leaves of transgenic *Nicotiana benthamiana* plants expressing the RCNMV MP [MP(+) plants; A. A. Vaewhongs and S. A. Lommel, *Virology* 212, 607 (1995)]. However, CP was not detected from these RNA-1 infections. CP accumulation and subsequent systemic infection was observed only when RNA-1 was co-inoculated with wild-type RNA-2 or mutant RNA-2 transcripts which were incapable of MP synthesis.

An RCNMV RNA-1 cDNA clone, from which infectious transcripts can be synthesized (Z. Xiong and S. A. Lommel, *Virology* 182, 388 (1991)), was engineered to express a synthetic mutant form of the *Aequorea victoria* green fluorescent protein (SGFP; W. L. Chiu, Y. Niwa, W. Zeng, T. Hirano, H. Kobayashi, J. Sheen, *Curr. Biol.* 6, 325 (1996)) in place of the CP [clone R1sGFP; see FIG. 1A]. The sGFP sequence was amplified via PCR from plasmid blue-sGFP-TYG-nos KS (kindly supplied by J. Sheen) using the following primers: GTCCATGGGATCGATGCATCATCAT-CATCATCATGTGAGCAAGGGCGAGGAGCTG (SEQ ID NO: 3) (codes for 6 non-template His residues) and GCTCTAGACGCGTTACTTGTACAGCTCGTCC (SEQ ID NO: 4). The amplified product was cleaved with ClaI/MluI and ligated into the infectious cDNA clone of RCNMV RNA-1 resulting in clone R1sGFP. Infectious T7 RNA polymerase transcripts were synthesized in vitro and mechanically inoculated onto plants. Plants were inspected for sGFP expression 1–3 days post-inoculation. All inoculations were repeated a minimum of three times on both *N. benthamiana* and *N. clevelandii* with at least two independent constructs. Experiments specific for MP(+) plants were repeated a minimum of three times with at least two independent constructs. All plants were maintained in a 20° C. glasshouse with ambient lighting.

Surprisingly, inoculation of R1sGFP transcripts onto MP(+) plants lead to the accumulation of detectable levels of sGFP only when wild-type or mutant RNA-2 transcripts were also present in the inoculum. RNA-2 transcripts from the related Dianthoviruses carnation ringspot virus (CRSV; T. L. Kendall and S. A. Lommel, *J. Gen. Virol* 73, 2479 (1992); T. L. Sit and S. A. Lommel, unpublished data) and sweet clover necrotic mosaic virus (SCNMV; Z. Ge, C. Hiruki, K. L. Roy, *J. Gen. Virol.* 73, 2483 (1992); Z. Ge and C. Hiruki, *Proc. Japan Acad.* 69, 113 (1993); SCNMV RNA-2 infectious cDNA clone kindly provided by T. Okuno) also induced sGFP expression. These findings suggested that a conserved region of RNA-2 was required to elicit efficient transcription of sgRNA from RNA-1.

Figure 1B:
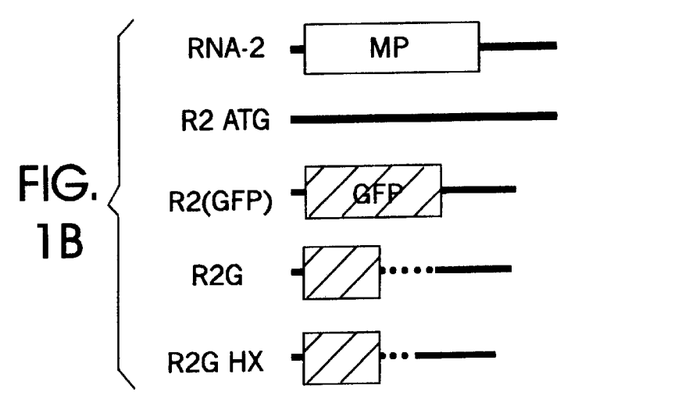

A chimeric RNA-2 clone with the wild-type GFP coding sequence in place of the MP sequence [clone R2(GFP); see FIG. 1B; (The wild-type GFP sequence in plasmid pGFP (kindly supplied by G. A. Payne) was cleaved with AgeI, blunted with Klenow and subsequently cleaved with SpeI. This GFP fragment was inserted into the infectious cDNA clone of RCNMV RNA-2 which had been cleaved with NcoI, blunted with Klenow and subsequently cleaved with XbaI. This resulted in clone R2(GFP). Clone R2GΔH was produced by cleavage of R2(GFP) with HpaI (within the GFP coding sequence) and HindIII (within multiple cloning site of plasmid) followed by insertion of the ApaLI/HindIII fragment from wild-type RCNMV RNA-2. Clone R2GΔHX was produced by cleavage of clone R2GΔH with BglII/XbaI followed by Klenow treatment and re-ligation to yield a 120-nucleotide deletion.)] was unable to replicate to detectable levels on MP(+) plants when co-inoculated with wild-type RNA-1 transcripts. Removal of the 3' terminal 225 nucleotides from the GFP sequence followed by replacement with the 3' terminal 324 nucleotides from the MP coding sequence [clone R2GΔH; see FIG. 1B] restored RNA-2 replication function. Co-incidentally, this replicaion competent RNA-2 was also able to elicit sGFP expression when co-inoculated with R1sGFP transcripts. This suggested that the 324-nucleotide region contained cis-acting elements required for RNA-2 replication along with trans-acting sequences required for eliciting RNA-1 sgRNA synthesis. Deletion of the 3' terminal 120 nucleotides of the MP ORF from clone R2GΔH (clone R2GΔHX) abolished replication of this RNA-2 construct forcing us to utilize an alternate strategy for delimiting the trans-acting sequences.

Figure 2A:
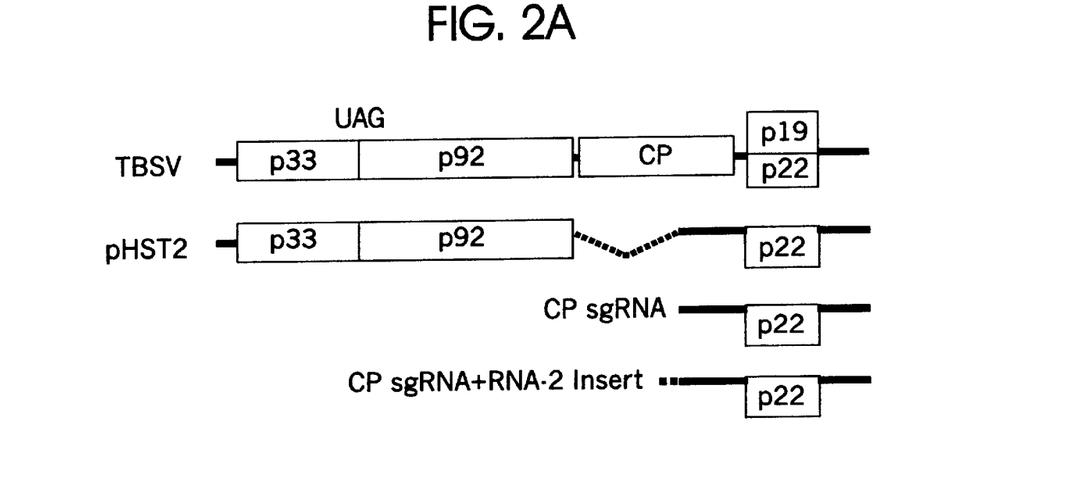
FIG. 2A. Map of the wild-type TBSV genome, TBSV expression vector pHST2 and the CP subgenomic RNA (sgRNA) it produces that was engineered to accept and express foreign genes. Deleted region of TBSV CP in pHST2 is indicated by dotted line. RCNMV RNA-2 insert position within the sgRNA is indicated by a dotted line.
Figure 2B:
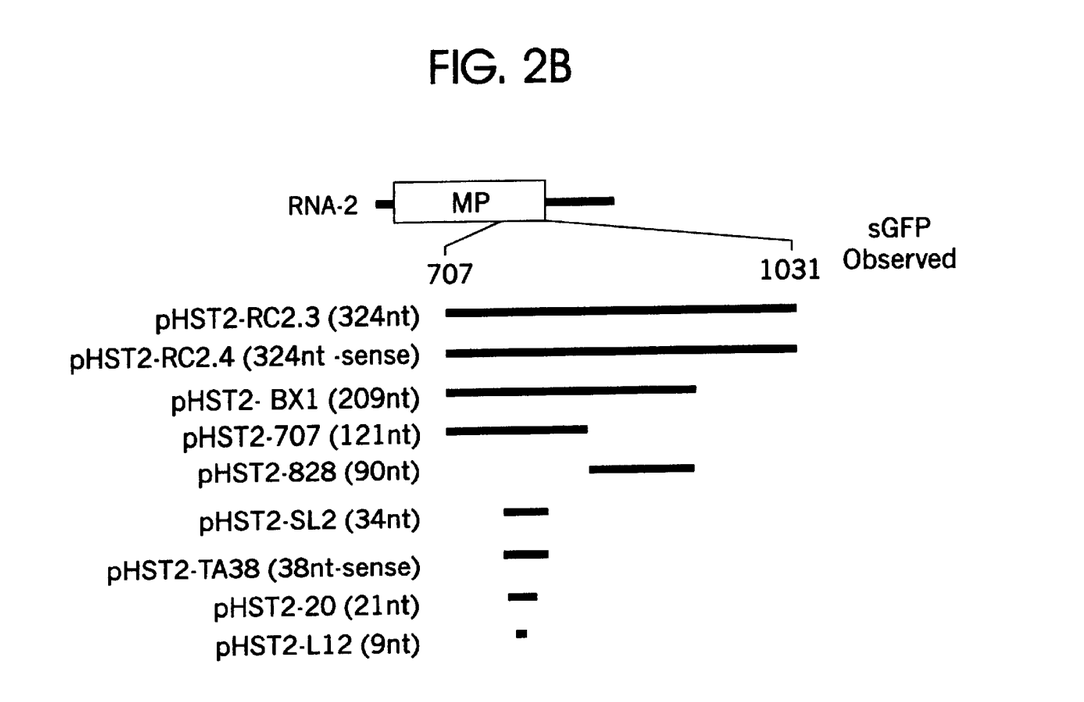
FIG. 2B. Maps of RNA-2 sequences that were inserted into the TBSV replicon and the ability of the RNA-2 sequence element to trans-activate sGFP expression when co-inoculated with R1sGFP.
Figure 3A:
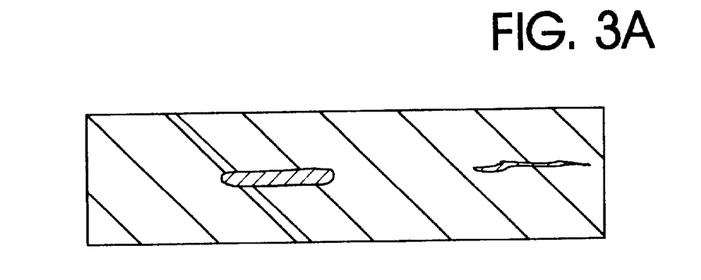
Figure 3B:
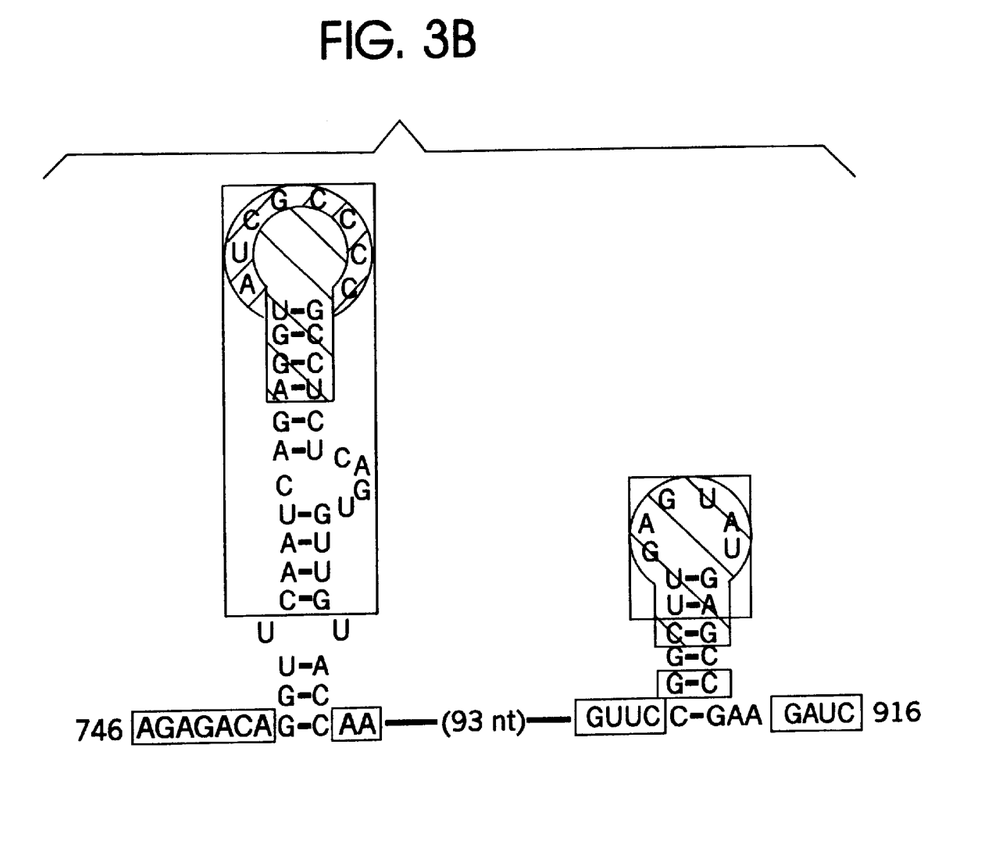
FIG. 3B. Partial sequence, predicted secondary structure, and conserved regions within the 209-nucleotide RCNMV RNA-2 region possessing trans-activator activity. Identical nucleotides between RCNMV and CRSV are shaded in gray, and with SCNMV are boxed. The vertical bracket identifies the core essential 34-nucleotide trans-activator. The reverse highlighted loop is complementary to an 8-nucleotide element on RNA-1. Indicated RNA-2 sequence is located between nucleotides 746 and 916.
Figure 3C:
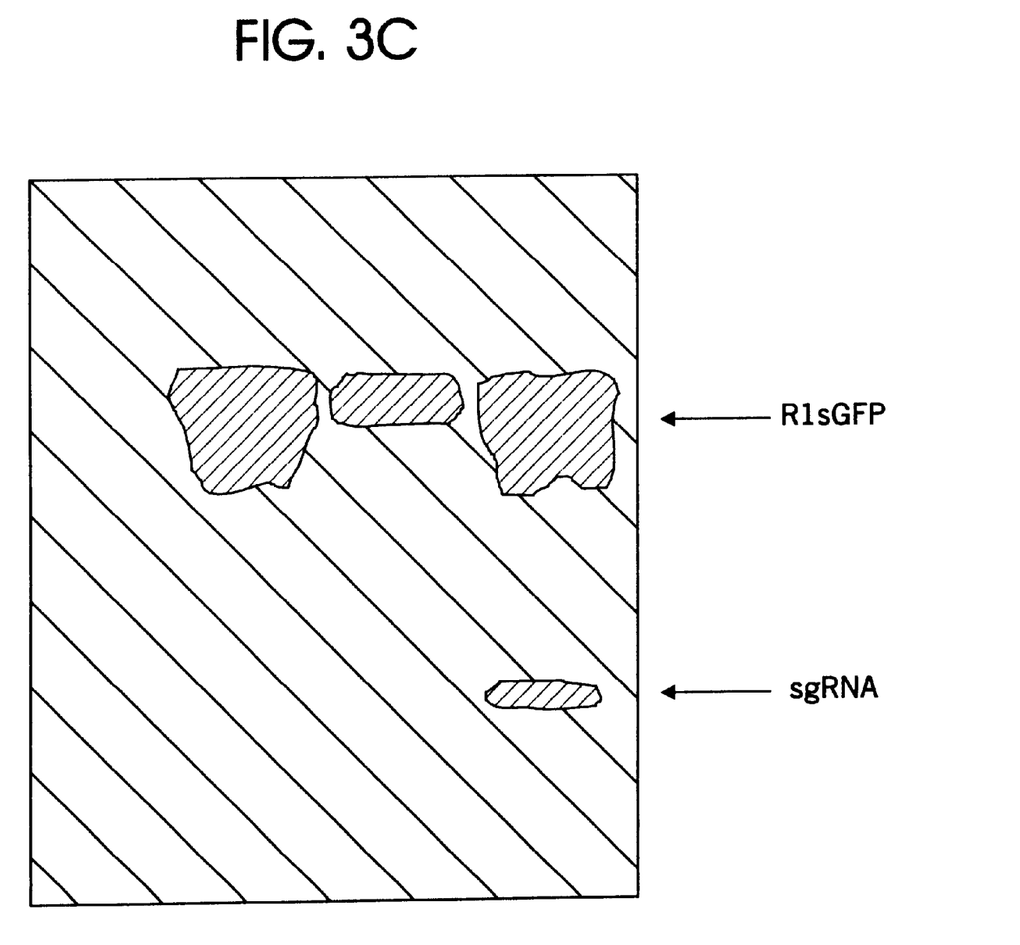
Figure 4A:
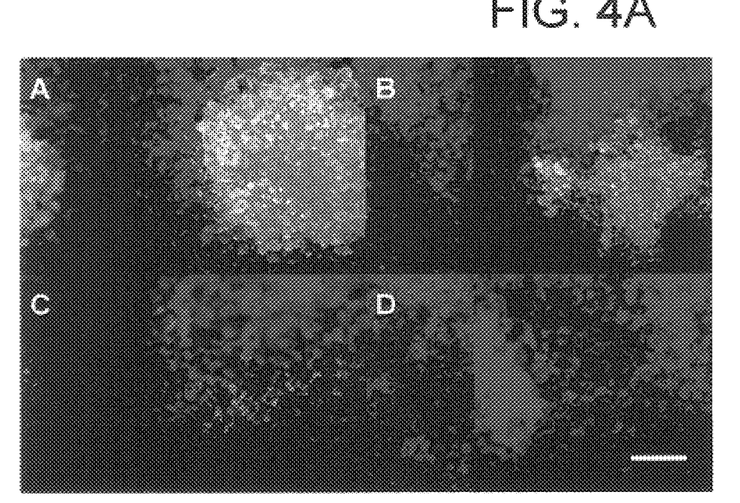
FIG. 4A. R1sGFP co-inoculations with RNA-2 or various pHST2 constructs. Panels: A—R1sGFP+wild-type RNA-2; B—R1sGFP+pHST2-SL2 (34 nt insert); C—R1sGFP+ pHST2-20 (20 nt insert); D—R1sGFP+pHST2-L12 (9 nt insert). The predicted structures of the RNA-2 inserts are shown below. Bar represents 0.4 mm.
Figure 4B:
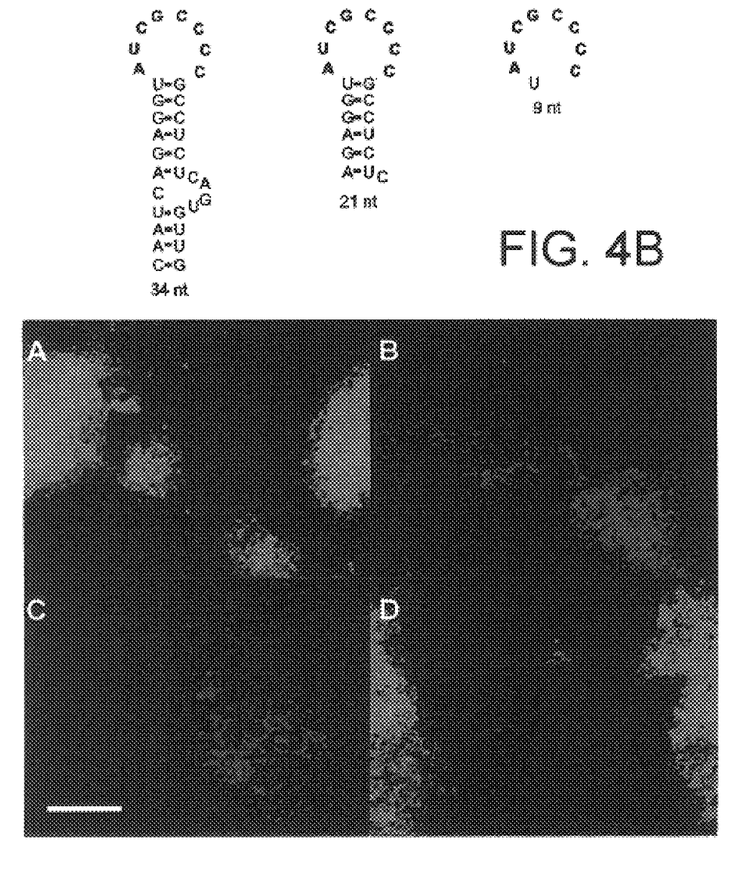
FIG. 4B. Co-inoculations with R1sGFP/pHST2-SL2 compensatory mutants. Panels: A—R1sGFP+pHST2-SL2; B—R1sGFP-M+pHST2-SL2; C—R1sGFP+pHST2-SL2-M; D—R1sGFP-M+pHST2-SL2-M. Bar represents 0.5 mm.

In order to uncouple trans-acting sequences required for RCNMV sgRNA expression from cis-acting sequences required for RNA-2 replication, a heterologous RNA viral vector was employed. An infectious cDNA clone of the monopartite tomato bushy stunt virus (TBSV) was previously engineered to allow transcription of foreign sequences from the CP subgenomic promoter (Plasmid pHST2; H. B. Scholthof, K.-B. G. Scholthof, A. O. Jackson, Annu. Rev. Phytopathology 34, 299 (1996); see FIG. 2A). The 324-nucleotide fragment from RCNMV RNA-2, possessing the trans-activator activity, was cloned into the TBSV vector (in both the genomic and complementary-sense orientation (see FIG. 2B; The RNA-2 fragment was excised from the infectious cDNA clone with ApaLI/XbaI followed by Klenow treatment and ligation into the SnaBI site of pHST2 to yield clones pHST2-RC2.3 (+) and -RC2.4 (−). The 209 nucleotide RNA-2 insert was produced by digestion of pHST2-RC2.3 with BglII/XbaI followed by Klenow treatment and re-ligation to yield clone pHST2-ΔBX.). Transcripts of these constructs were co-inoculated with R1sGFP transcripts onto N. benthamiana and Nicotiana clevelandii plants. sGFP expression was induced only when the RNA-2 insert was present and in the RCNMV genomic-sense orientation.

A smaller 209-nucleotide RCNMV RNA-2 insert (representing the sequence present in clone R2GΔHX) in the TBSV vector also induced sGFP expression when co-inoculated with R1sGFP transcripts. CP was expressed when this TBSV construct was co-inoculated with wild-type RCNMV RNA-1 transcripts (see FIG. 3A). This suggests that the trans-activation effect is not gene specific and that sGFP is a valid reporter to identify and delimit the cis- and trans-acting signals for CP sgRNA synthesis. Based on alignments with the CRSV and SCNMV RNA-2 sequences, in conjunction with a computer-predicted secondary structure model of the 209-nucleotide RCNMV RNA-2 sequence, two conserved stem-loop structures were predicted (see FIG. 3B. Inserts from the regions containing each predicted stem-loop were tested separately for their ability to trans-activate sGFP expression. Only the TBSV replicon containing the 5' terminal 120 nucleotides from this region of RNA-2 (The 5' and 3' terminal regions of the 209-nucleotide element were amplified via PCR with the following primers: 5' terminus with GTCGACGCGTGCACCAAATCCAATGTG (SEQ ID NO: 5) and CTCGAGCTGTTTCAACACCTTGGAC (SEQ ID NO: 6) and the 3' terminus with TACGTAAAGGAGGAACTGGCAGC (SEQ ID NO: 7) and CTCGAGATCTTCGGCTCATACTC (SEQ ID NO: 8). The amplified fragments were cleaved with SnaBI/XhoI and ligated into similarly cleaved pHST2.) was capable of inducing sGFP expression from co-inoculated R1sGFP transcripts (see FIG. 2B).

The highly conserved 34-nucleotide stem-loop sequence within this 120-nucleotide region (see FIG. 3B) was the next focus. The 34-nucleotide RNA-2 sequence expressed from the TBSV replicon in the genomic but not the complementary-sense orientation (RCNMV RNA-2 inserts were produced by first annealing the following phosphorylated complementary oligonucleotides: 34-nucleotide insert GTATCGATCAATCAGAGGTATCGCCCCGCCTCTCAGTGTTGC (SEQ ID NO: 9) and TCGAGCAACACTGAGAGGCGGGGCGATACCTCTGATTGATCGATAC (SEQ ID NO: 10); 21-nucleotide insert GTAAGCTTAGAGGTATCGCCCCGCCTC (SEQ ID NO: 11) and TCGAGAGGCGGGGCGATACCTCTAAGCTTAC (SEQ ID NO: 12); 9-nucleotide insert GTATCGCCCCTGCAGC (SEQ ID NO: 13) and TCGAGCTGCAGGGGCGATAC (SEQ ID NO: 14); negative genomic orientation 38-nucleotide insert GTACAACACTGAGAGGCGGGGCGATACCTCTGATTGAATCGATC (SEQ ID NO: 15) and TCGAGATCGATTCAATCAGAGGTATCGCCCCGCCTCTCAGTGT-TGTAC (SEQ ID NO: 16); 34-nucleotide insert with mutations in the loop sequence (nucleotide changes underlined) GTATCGATCAATCAGAGGTA<u>A</u>CG<u>G</u>CC<u>G</u>GCCTCTCAGTGTTGC (SEQ ID NO: 17) and AGCAACACTGAGAGGC<u>C</u>GG<u>C</u>CG<u>T</u>TACCTCTGATTGATCGATAC (SEQ ID NO: 18). The resulting double-stranded DNAs were ligated into pHST2 cleaved with SnaBI/XhoI.) was sufficient for sGFP expression at levels near those obtained by wild-type RNA-2 co-inoculation (see FIG. 4A). Northern blot hybridization analysis showed that the sgRNA containing the sGFP sequence is produced only when the 34-nucleotide RNA-2 sequence is present (see FIG. 3C). The terminal 21 nucleotides of the stem-loop structure (see FIG. 4A), conserved among the Dianthoviruses, also elicited sGFP expression but at a much lower level. However, a 9-nucleotide insert containing the 8 nucleotides comprising the loop of the 34-nucleotide element, was not sufficient to induce visible sGFP expression (FIG. 4A).

Sequence alignments revealed that the 8-nucleotide loop from RNA-2 is complementary to an 8-nucleotide sequence element on RNA-1 located 2 nucleotides upstream from the start site of sgRNA synthesis and within a region broadly mapped to be the CP subgenomic promoter (S. K. Zavriev, C. M. Hickey, S. A. Lommel, *Virology* 216, 407 (1996)). To determine if there was a direct RNA-RNA interaction between these two sequences, the 8-nucleotide element on RNA-1 was mutated at three positions (that would not alter the amino acid coding sequence of the p88 polymerase) to produce clone R1sGFP-M (PCR-based mutagenesis of the RNA-1 sequence was performed as in S. Li, M. F. Wilkinson, *BioTechniques* 23, 588 (1997) utilizing the following primers: mutagenic primer (altered nucleotides are underlined) GTAGGTAATACGTTTGTTGA<u>A</u>CG<u>G</u>CC<u>G</u>TCACAAG (SEQ ID NO: 19); upstream primer CTGTCGATGTACTCGAGAAG (SEQ ID NO: 20); downstream primer GTGTTATCT-GCAACGAAGCG (SEQ ID NO: 21). After amplification, the PCR product was gel-purified, cleaved with XhoI/BglII and ligated into similarly cleaved R1sGFP to generate clone R1sGFP-M.). Co-inoculation of R1sGFP-M transcripts with TBSV transcripts containing the 34-nucleotide RNA-2 trans-activator element did not elicit detectable sGFP synthesis (see FIG. 4B, Panel B). When compensatory mutations were incorporated into the loop sequence of the 34-nucleotide RNA-2 element to restore complementarity with the mutated RNA-1 element (pHST2-SL2-M), sGFP expression was restored (see FIG. 4B, Panel D and Table 1).

TABLE 1

Compensatory mutations between the predicted loop sequence of the RCNMV RNA-2 trans-activator and the complementary RCNMV RNA-1 8-nucleotide element in the CP subgenomic promoter restore sGFP expression.[1]

| RCNMV RNA-1/TBSV inoculum | RNA-1 8 nt element | RNA-2 TA loop sequence | sGFP produced |
|---|---|---|---|
| R1sGFP/pHST2-SL2 | GGGGCGAT (SEQ ID NO: 22) | ATCGCCCC (SEQ ID NO: 23) | + |
| R1sGFP-M/pHST2-SL2 | CGGCCGTT (SEQ ID NO: 24) | ATCGCCCC (SEQ ID NO: 25) | − |
| R1sGFP/pHST2-SL2-M | GGGGCGAT (SEQ ID NO: 26) | AACGGCCG (SEQ ID NO: 27) | − |
| R1sGFP-M/pHST2-SL2-M | CGGCCGTT (SEQ ID NO: 28) | AACGGCCG (SEQ ID NO: 29) | + |

[1]Co-inoculations of R1sGFP/R1sGFP-M with pHST2-SL2/pHST2-SL2-M were performed on both *Nicotiana benthamiana* and *Nicotiana clevelandii* in triplicate. Sequence changes are indicated in bold typeface. Leaves were examined for sGFP expression 3 days post inoculation.

These results establish that a 34-nucleotide sequence, predicted to form a simple stem-loop, trans-activates sgRNA synthesis on another RNA. Furthermore, mutation data supports the conclusion that trans-activation is accomplished by base-pairing between the 8-nucleotide loop region of the RNA-2 trans-activator and an 8-nucleotide element within the CP subgenomic promoter on RNA-1. At this time, it is uncertain whether RNA-1 and RNA-2 can interact directly by themselves or whether they require other viral and/or host proteins to stabilize this interaction. Sequence elements nearly identical to the RCNMV RNA-1 8-nucleotide element are also present at the same location on the RNA-1's of CRSV and SCNMV. This phylogenetic conservation of RNA-1 and RNA-2 sequences would suggest a conserved mechanism for sgRNA synthesis among the Dianthoviruses.

Figure 5A:
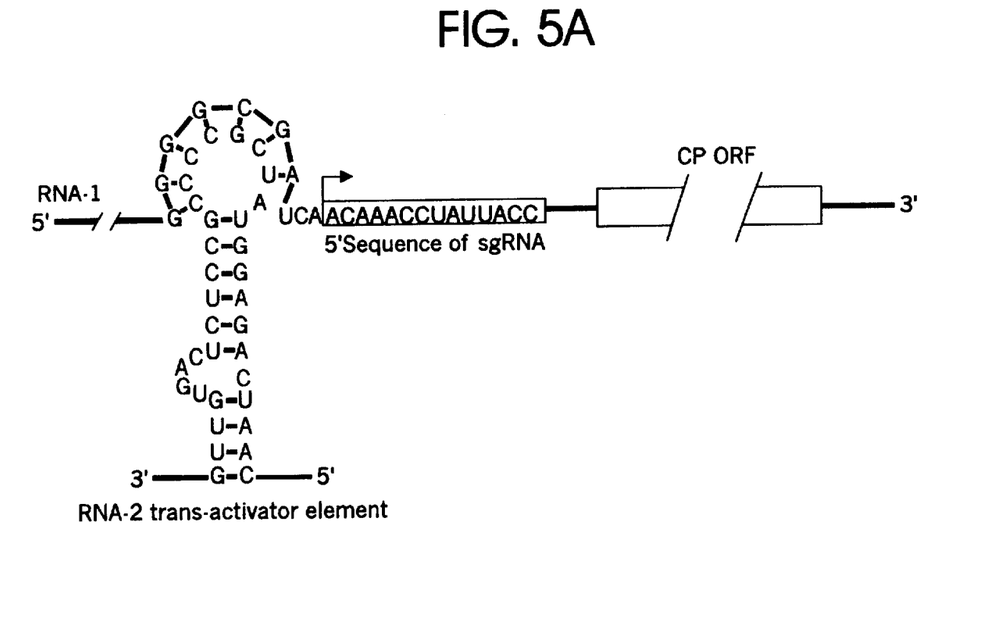
FIG. 5A. The loop region of the 34-nucleotide trans-activator is shown base-pairing with a complementary 8 nucleotide element, 2 nucleotides upstream from the CP sgRNA start site (right angle arrow) on RNA-1. The gray shaded 14-nucleotide sequence, representing the 5' terminus of the sgRNA, is nearly identical (13 out of 14 nucleotides) to the 5' terminal 14 nucleotides on genomic RNA-1 and is hypothesized to be the recognition site for polymerase to initiate complementary-strand synthesis.
Figure 5B:
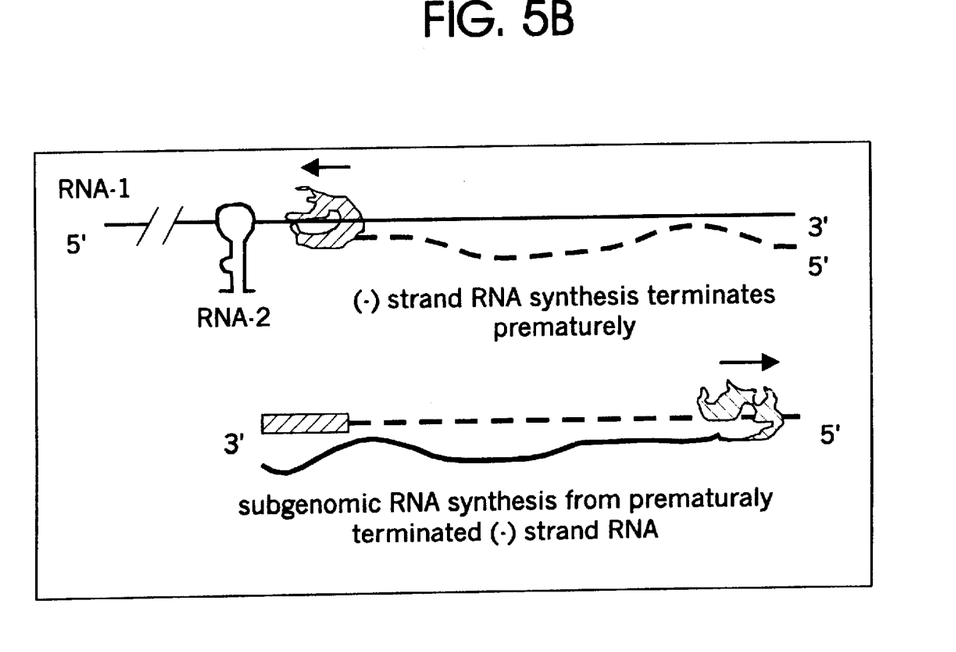

Without wishing to be bound by any one theory for the instant invention, the following model for sgRNA synthesis is proposed (see FIG. 5). During synthesis of the complementary strand of RNA-1 within the early phase of replication, in the absence of high levels of RNA-2, the replicase produces full-length genomic-sense copies of RNA-1. Later during replication of progeny RNAs, when RNA-2 becomes abundant, the trans-activator element on RNA-2 binds to the 8-nucleotide element on RNA-1 to produce a structure that sterically prevents the replicase from completing the synthesis of full-length complementary-strands of RNA-1. Since the 5' terminal sequences of the genomic RNA-1 and the sgRNA are highly conserved, this truncated complementary strand RNA may serve as a template for replication to produce the genomic-sense sgRNA which is the translational template for CP. The presence of a double-stranded RNA species in RCNMV infected tissue, corresponding in size to this replicative intermediate, supports this model (T. A. M. Osman and K. W. Buck, *J. Gen. Virol.* 71, 945 (1990)). This mechanism for controlling the temporal expression of CP may have evolved to ensure that sufficient quantities of RNA-1 and RNA-2 are present prior to the commencement of virion assembly. This model for sgRNA synthesis differs from that proposed for most RNA plant viruses, as exemplified by brome mosaic virus (BMV). BMV sgRNA synthesis is initiated by binding of the viral polymerase complex to an internal sequence on the negative strand template followed by transcription of positive stranded mRNA for the CP (termed RNA 4; W. A. Miller, T. W. Dreher, T. C. Hall, *Nature* 313, 68 (1985)). Recent findings have shown that the binding of the BMV polymerase is dependent on the sequence, but not the structure, of the RNA template (R. W. Siegel, S. Adkins, C. C. Kao, *Proc. Natl. Acad. Sci. USA* 94, 11238 (1997)).

The foregoing is illustrative of the present invention, and is not to be construed as limiting thereof. The invention is defined by the following claims, with equivalents of the claims to be included therein.

We claim:

1. A method of activating transcription of an RNA of interest in a dicot cell, said method comprising:
   (a) providing a dicot host cell comprising a heterologous construct, the heterologous construct comprising a Dianthovirus subgenomic promoter operatively associated with a heterologous RNA of interest,
      wherein said promoter does not initiate transcription of said heterologous RNA in the absence of a Dianthovirus trans-activating RNA segment,
      and wherein said Dianthovirus trans-activating RNA segment is absent from said host cell; and then
   (b) introducing a Dianthovirus trans-activating nucleic acid segment into said host cell so that transcription of said heterologous RNA is initiated.

2. A method according to claim 1, wherein said cell is in vitro.

3. A method according to claim 1, wherein said cell is in vivo in a tissue or plant.

4. A method according to claim 1, wherein said Dianthovirus is selected from the group consisting of red clover necrotic mosaic virus, carnation ringspot virus, sweet clover necrotic mosaic virus, and furcraea necrotic streak virus.

5. A method according to claim 1, wherein said subgenomic promoter is a capsid protein promoter.

6. A method according to claim 1, wherein said trans-activating RNA segment is not greater than 50 nucleotides in length.

7. A method according to claim 1, wherein said trans-activating RNA segment is introduced into said cell by electroporation.

8. A method according to claim 1, wherein said trans-activating RNA segment is introduced into said cell by infecting said cell with a virus, which virus expresses said trans-activating RNA.

9. A method of activating transcription of an RNA of interest in a dicot plant, said method comprising:

(a) transforming a plant cell with a vector comprising a heterologous construct, the heterologous construct comprising a Dianthovirus subgenomic promoter operatively associated with a heterologous nucleic acid of interest to provide a transformed plant cell, wherein said promoter does not initiate transcription of said heterologous nucleic acid in the absence of a Dianthovirus trans-activating RNA segment, and wherein said Dianthovirus trans-activating RNA segment is absent from said plant cell; then (b) regenerating a plant from said transformed plant cell; and then (c) infecting said plant with a viral or bacterial vector that transcribes said trans-activating RNA segment in the cells of said plant so that transcription of said heterologous nucleic acid in the cells of said plant is initiated.

10. A method according to claim 9, wherein said transforming step is carried out with a ballistic vector.

11. A method according to claim 9, wherein said transforming step is carried out by electroporation.

12. A method according to claim 9, wherein said transforming step is carried out with an Agrobacterium vector.

13. A method according to claim 9, wherein said transforming step is carried out with a DNA virus vector.

14. A method according to claim 9, wherein said infecting step is carried out with an RNA virus vector, a DNA virus vector, or an Agrobacterium vector.

15. A method of activating transcription of an RNA of interest in a dicot cell, said method comprising:

(a) providing a dicot cell comprising a first heterologous construct and a second heterologous construct;

the first heterologous construct comprising an inducible promoter operably associated with a nucleic acid segment encoding a Dianthovirus trans-activating segment;

the second heterologous construct comprising a Dianthovirus subgenomic promoter operatively associated with the heterologous RNA of interest, wherein said Dianthovirus subgenomic promoter does not initiate transcription of said heterologous RNA of interest in the absence of said Dianthovirus transactivating RNA segment and initiates transcription of said heterologous RNA in the presence of said Dianthovirus trans-activating RNA segment; and then (b) inducing said inducible promoter so that transcription of said Dianthovirus trans-activating regulatory element is initiated, and transcription of said heterologous RNA in said cell is initiated.

16. A method according to claim 15, wherein said cell is in vitro.

17. A method according to claim 15, wherein said cell is in vivo in a tissue or plant.

18. A method according to claim 15, wherein said Dianthovirus is selected from the group consisting of red clover necrotic mosaic virus, carnation ringspot virus, sweet clover necrotic mosaic virus, and furcraea necrotic streak virus.

19. A method according to claim 15, wherein said subgenomic promoter is a capsid protein promoter.

20. A method according to claim 15, wherein said trans-activating RNA segment is not greater than 50 nucleotides in length.

21. A method according to claim 15, wherein said inducible promoter is a nematode responsive promoter, wherein said dicot cell is in vivo in a plant, and said RNA of interest encodes a product disruptive of nematode attack on said dicot cell.

22. A transgenic dicot plant comprising transformed plant cells, said transformed plant cells comprising a first heterologous construct and a second heterologous construct;

said first heterologous construct comprising an inducible promoter operably associated with a nucleic acid segment encoding a Dianthovirus trans-activating segment;

said second heterologous construct comprising a Dianthovirus subgenomic promoter operatively associated with said heterologous RNA of interest, wherein said Dianthovirus subgenomic promoter does not initiate transcription of said heterologous RNA of interest in the absence of said Dianthovirus trans-activating RNA segment and initiates transcription of said heterologous RNA in the presence of said Dianthovirus trans-activating RNA segment;

whereby inducing said inducible promoter causes transcription of said Dianthovirus trans-activating regulatory element to be initiated, so that transcription of said heterologous RNA is initiated.

23. A transgenic plant according to claim 22, which heterologous RNA of interest encodes a protein or peptide.

24. A transgenic plant according to claim 22, which heterologous RNA of interest encodes a mammalian protein or peptide.

25. A transgenic plant according to claim 22, wherein said inducible promoter is a nematode responsive promoter, and said RNA of interest encodes a product disruptive of nematode attack.

26. A seed that germinates into a transgenic plant according to claim 22.

27. An isolated nucleic acid selected from the group consisting of:

(a) an RNA consisting of the sequence:
UCAAUCAGAGGUAUCGCCCCGCCUCU-CAGUGUUG (SEQ ID NO: 1)

(b) an RNA consisting of the sequence:
AGAGGUAUCGCCCCGCCUCUC (SEQ ID NO:2);

(c) a DNA encoding an RNA of (a) above and (d) a DNA encoding an RNA of (b) above.

28. A construct comprising an isolated nucleic acid according to claim 27 operatively associated with a heterologous promoter.

29. A vector carrying a construct according to claim 28.

* * * * *

SEQUENCE LISTING

<160> NUMBER OF SEQ ID NOS: 29

<210> SEQ ID NO 1
<211> LENGTH: 34
<212> TYPE: RNA
<213> ORGANISM: Artificial Sequence
<220> FEATURE:
<223> OTHER INFORMATION: Description of Artificial Sequence:AN RNA TRANS-ACTIVATING SEQUENCE

<400> SEQUENCE: 1
ucaaucagag guaucgcccc gccucucagu guug    34

```
<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence:RNA
      TRANS-ACTIVATOR

<400> SEQUENCE: 2
agagguaucg ccccgccucu c                                              21

<210> SEQ ID NO 3
<211> LENGTH: 55
<212> TYPE: DNA
<213> ORGANISM: Artificial Sequence
<220> FEATURE:
<223> OTHER INFORMATION: Description of Artificial Sequence:PRIMER

<400> SEQUENCE: 3
gtccatggga tcgatgcatc atcatcatca tcatgtgagc aagggcgagg agctg         55

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence:PRIMER

<400> SEQUENCE: 4
gctctagacg cgttacttgt acagctcgtc c                                   31

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:PRIMER

<400> SEQUENCE: 5
gtcgacgcgt gcaccaaatc caatgtg                                        27

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:PRIMER

<400> SEQUENCE: 6
ctcgagctgt ttcaacacct tggac                                          25

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:PRIMER

<400> SEQUENCE: 7
tacgtaaagg aggaactggc agc                                            23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:PRIMER
```

<400> SEQUENCE: 8
ctcgagatct tcggctcata ctc                                          23

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence:INSERT

<400> SEQUENCE: 9
gtatcgatca atcagaggta tcgccccgcc tctcagtgtt gc                     42

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence:INSERT

<400> SEQUENCE: 10
tcgagcaaca ctgagaggcg gggcgatacc tctgattgat cgatac                 46

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:INSERT

<400> SEQUENCE: 11
gtaagcttag aggtatcgcc ccgcctc                                      27

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence:INSERT

<400> SEQUENCE: 12
tcgagaggcg gggcgatacc tctaagctta c                                 31

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence:INSERT

<400> SEQUENCE: 13
gtatcgcccc tgcagc                                                  16

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:INSERT

<400> SEQUENCE: 14
tcgagctgca ggggcgatac                                              20

<210> SEQ ID NO 15

```
<211> LENGTH: 44
<212> TYPE: DNA
<213> ORGANISM: Artificial Sequence
<220> FEATURE:
<223> OTHER INFORMATION: Description of Artificial Sequence:INSERT

<400> SEQUENCE: 15
gtacaacact gagaggcggg gcgatacctc tgattgaatc gatc                    44

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence:INSERT

<400> SEQUENCE: 16
tcgagatcga ttcaatcaga ggtatcgccc cgcctctcag tgttgtac                48

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence:INSERT

<400> SEQUENCE: 17
gtatcgatca atcagaggta acggccggcc tctcagtgtt gc                      42

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence:INSERT

<400> SEQUENCE: 18
agcaacactg agaggccggc cgttacctct gattgatcga tac                     43

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:MUTAGENIC
      PRIMER

<400> SEQUENCE: 19
gtaggtaata cgtttgttga acggccgtca caag                               34

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:PRIMER

<400> SEQUENCE: 20
ctgtcgatgt actcgagaag                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:PRIMER
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:MODIFIED
      LOOP SEQUENCE

<400> SEQUENCE: 21
gtgttatctg caacgaagcg                                              20

<210> SEQ ID NO 22
<211> LENGTH: 8
<212> TYPE: DNA
<213> ORGANISM: Artificial Sequence
<220> FEATURE:
<223> OTHER INFORMATION: Description of Artificial Sequence:MODIFIED
      LOOP SEQUENCE

<400> SEQUENCE: 22 ggggcgat                                                            8

<210> SEQ ID NO 23
<211> LENGTH: 8
<212> TYPE: DNA
<213> ORGANISM: Artificial Sequence
<220> FEATURE:
<223> OTHER INFORMATION: Description of Artificial Sequence:MODIFIED
      LOOP SEQUENCE

<400> SEQUENCE: 23 atcgcccc                                                            8

<210> SEQ ID NO 24
<211> LENGTH: 8
<212> TYPE: DNA
<213> ORGANISM: Artificial Sequence
<220> FEATURE:
<223> OTHER INFORMATION: Description of Artificial Sequence:MODIFIED
      LOOP SEQUENCE

<400> SEQUENCE: 24 cggccgtt                                                            8

<210> SEQ ID NO 25
<211> LENGTH: 8
<212> TYPE: DNA
<213> ORGANISM: Artificial Sequence
<220> FEATURE:
<223> OTHER INFORMATION: Description of Artificial Sequence:MODIFIED
      LOOP SEQUENCE

<400> SEQUENCE: 25 atcgcccc                                                            8

<210> SEQ ID NO 26
<211> LENGTH: 8
<212> TYPE: DNA
<213> ORGANISM: Artificial Sequence
<220> FEATURE:
<223> OTHER INFORMATION: Description of Artificial Sequence:MODIFIED
      LOOP SEQUENCE

<400> SEQUENCE: 26 ggggcgat                                                            8

<210> SEQ ID NO 27
<211> LENGTH: 8
<212> TYPE: DNA
<213> ORGANISM: Artificial Sequence
<220> FEATURE:
<223> OTHER INFORMATION: Description of Artificial Sequence:MODIFIED
      LOOP SEQUENCE

<400> SEQUENCE: 27

```
aacggccg                                                             8

<210> SEQ ID NO 28
<211> LENGTH: 8
<212> TYPE: DNA
<213> ORGANISM: Artificial Sequence
<220> FEATURE:
<223> OTHER INFORMATION: Description of Artificial Sequence:MODIFIED
      LOOP SEQUENCE

<400> SEQUENCE: 28 cggccgtt                                                             8

<210> SEQ ID NO 29
<211> LENGTH: 8
<212> TYPE: DNA
<213> ORGANISM: Artificial Sequence
<220> FEATURE:
<223> OTHER INFORMATION: Description of Artificial Sequence:MODIFIED
      LOOP SEQUENCE

<400> SEQUENCE: 29 aacggccg                                                             8
```